United States Patent [19]

Schoendorfer

[11] Patent Number: 5,676,144
[45] Date of Patent: Oct. 14, 1997

[54] METHOD AND APPARATUS FOR DETERMINATION OF CHEMICAL SPECIES IN BODY FLUID

[75] Inventor: Donald W. Schoendorfer, Santa Ana, Calif.

[73] Assignee: Sudor Partners, Santa Ana, Calif.

[21] Appl. No.: 483,504

[22] Filed: Jun. 7, 1995

Related U.S. Application Data

[63] Continuation of Ser. No. 94,787, Jul. 20, 1993, Pat. No. 5,465,713, which is a continuation-in-part of Ser. No. 39,631, Mar. 30, 1993, Pat. No. 5,438,984, which is a continuation-in-part of Ser. No. 989,204, Dec. 11, 1992, Pat. No. 5,441,048, which is a continuation-in-part of Ser. No. 569,007, Aug. 15, 1990, Pat. No. 5,203,327, which is a continuation-in-part of Ser. No. 241,707, Sep. 8, 1988, Pat. No. 4,957,108.

[51] Int. Cl.$^6$ ........................................... A61B 5/00
[52] U.S. Cl. ........................ 128/632; 128/636; 128/760; 128/771
[58] Field of Search ........................ 128/632, 636, 128/759, 760, 771; 604/312

[56] References Cited

U.S. PATENT DOCUMENTS

| | | |
|---|---|---|
| Re. 32,026 | 11/1985 | Yamashita . |
| 2,821,733 | 4/1958 | Peck . |
| 3,552,929 | 1/1971 | Fields et al. . |
| 3,976,049 | 8/1976 | Yamashita . |
| 4,190,060 | 2/1980 | Greenleaf et al. . |
| 4,266,556 | 5/1981 | Barlow et al. . |
| 4,287,153 | 9/1981 | Townsend . |
| 4,329,999 | 5/1982 | Phillips . |
| 4,341,207 | 7/1982 | Steer et al. . |
| 4,360,015 | 11/1982 | Mayer . |
| 4,401,122 | 8/1983 | Clark, Jr. . |
| 4,444,193 | 4/1984 | Fogt et al. . |
| 4,542,751 | 9/1985 | Webster et al. . |
| 4,595,011 | 6/1986 | Phillips . |
| 4,631,174 | 12/1986 | Kondo . |
| 4,667,665 | 5/1987 | Blanco et al. . |
| 4,706,676 | 11/1987 | Peck . |
| 4,732,153 | 3/1988 | Phillips . |
| 4,756,314 | 7/1988 | Eckenhoff et al. . |
| 4,775,361 | 10/1988 | Jacques et al. . |
| 4,909,256 | 3/1990 | Peck . |
| 4,957,108 | 9/1990 | Schoendorfer et al. . |
| 4,960,467 | 10/1990 | Peck . |
| 5,036,861 | 8/1991 | Sembrowich et al. . |

(List continued on next page.)

FOREIGN PATENT DOCUMENTS

| | | |
|---|---|---|
| 0099748 | 2/1984 | European Pat. Off. . |
| 0217403 | 4/1987 | European Pat. Off. . |
| 0135646 | 6/1986 | Japan . |
| 2157955 | 11/1985 | United Kingdom . |
| WO8904630 | 6/1989 | WIPO . |

OTHER PUBLICATIONS

Jackson, A.P., et al., "Two-site monoclonal antibody assays for human heart- and brain-type creatine kinase", Clinical Chemistry, vol. 30, No. 7, pp. 1157–1162, 1984.

(List continued on next page.)

*Primary Examiner*—Lee S. Cohen
*Attorney, Agent, or Firm*—Knobbe, Martens, Olson & Bear

[57] ABSTRACT

Disclosed is a method and apparatus for the non-invasive determination of one or more preselected analytes in a body fluid expressed through the skin. The fluid is collected in a dermal concentration patch and concentrated by driving off a portion of the substantial water fraction under the influence of body heat. The analyte is optimally complexed with an immobilized specific binding partner and an indicium of the presence of the analyte is visually expressed. The patch may comprise a plurality of test zones for screening for a plurality of analytes. Additional positive and negative control zones are also disclosed. The patch may comprise a feature to detect tampering with the patch to produce false negative results, especially when used in screens for drugs of abuse. In addition to being useful as a drug of abuse screen, the patch is useful for diagnostic purposes.

18 Claims, 4 Drawing Sheets

U.S. PATENT DOCUMENTS

| | | |
|---|---|---|
| 5,076,273 | 12/1991 | Schoendorfer et al. . |
| 5,094,248 | 3/1992 | Kawam . |
| 5,131,390 | 7/1992 | Sakaguchi et al. . |
| 5,140,986 | 8/1992 | Klingner . |
| 5,203,327 | 4/1993 | Schoendorfer et al. . |
| 5,438,984 | 8/1995 | Schoendorfer . |
| 5,441,048 | 8/1995 | Schoendorfer . |

OTHER PUBLICATIONS

Howard, M.J., et al., eds., Films, Sheets, and Laminates, A Desk-Top Data Bank, The International Plastics Selector, Inc., San Diego, CA, pp. xli, B–269, B–296, B–358, B–524, B–893 (no author listed).

Abuscreen Radioimmunoassay for Cocaine Metabolite, Product Insert, Roche Diagnostic Systems, Inc., Nov. 1987, Nutley, New Jersey (numbers of relevant pages and author unknown).

Coat-A-Count Cocaine Matabolite, Product Insert, DPC Diagnostic Products Corporation, May 11, 1989, Los Angeles, California, pp. 1–13 (author unknown).

Weast, Robert C., ed., Handbook of Chemistry and Physics, 47th ed., 1966, p. C–247 (author unknown).

Phillips, M., et al., "Long-term sweat collection using salt-impregnated pads", The Journal of Investigative Dermatology, 68:221–224, 1977.

Darwin, et al., "Identification of Drug Analytes Excreted in Sweat after Cocaine and Heroin Administration", Abstract presented at 1993 Joint Meeting: Society of Forensic Toxicologists & California Association of Toxicologists, Aug.–Sep. 1993 (one page).

Hillsgrove, et al., "Kinetic Studies of Cocaine Excretion in Sweat", Abstract presented at 1993 Joint Meeting: Society of Forensic Toxicologists & California Association of Toxicologists, Aug.–Sep. 1993 (one page).

Burns, et al., "Use of a Skin Patch to Monitor Cocaine Abuse", Abstract presented at 1993 Joint Meeting: Society of Forensic Toxicologists & California Association of Toxicologists, Aug.–Sep. 1993 (one page).

Hillsgrove, et al., "Monitoring Cocaine Abuse with a Sweat Patch", Abstract presented at 1993 Joint Meeting: Society of Forensic Toxicologists & California Association of Toxicologists, Aug.–Sep. 1993 (one page).

Fay, et al., "Sweat Eluate Analysis for Cocaine, Benzoylecgonine, and Ecgonine Methyl Ester by STC Diagnostics Cocaine Micro–Plate EIA and GC/MS", Abstract presented at 1994 Annual Meeting of the American Academy of Forensic Sciences, Inc., Dec. 1993 (one page).

Kahn, Jason, "Sweat Collection Patch Could Aid in Monitoring Illicit Drugs", Clinical Chemistry News, vol. 20, No. 1, pp. 1 & 3, Jan. 1994.

Sutliff, Jacqueline, "Detecting Drugs in Perspiration", Technical Bulletin of PharmChem Laboratories, Inc., vol. 3, No. 2, Summer 1993 (2 pages).

Aly, Raza, Ph.D., et al., "Effect of Prolonged Occlusion on the Microbial Fluora, pH, Carbon Dioxide and Transepidermal Water Lost on Human Skin", The Journal of Investigative Dermatology, vol. 71, No. 6, 71:378–381 (1978).

Labaune, Jean–Pierre, Handbook of Pharmacokinetics: Toxicity Assessment of Chemicals, pp. 16–25, 1989.

Ashburn, Michael, M.D., et al., "Iontophoretic Delivery of Morphine for Postoperative Analgesia", Journal of Pain and Symptom Management, vol. 7, No. 1., p. 27 et seq., Jan. 1992.

Peck, Carl C., et al., "Continuous Transepidermal Drug Collection: Basis for Use in Assessing drug Intake and Pharmacokinetics", Journal of Pharmacokinetics and Biopharmacology, vol. 9, No. 1, pp. 41–58, 1981.

Odland, George F., "Structure of the Skin", Physiology, Biochemistry and Molecular Biology of the Skin, Lowell A. Goldsmith, M.D., editor, 2nd ed., pp. 3–62, 1991.

Shaw, Jane E., et al., "Percutaneous Absorption", Physiology, Biochemistry and Molecular Biology of the Skin, Lowell A. Goldsmith, M.D., editor, 2nd ed., pp. 1447–1479, 1991.

Sato, Kenzo, "Biology of Eccrine Sweat Glands", Physiology, Biochemistry and Molecular Biology of the Skin, Lowell A. Goldsmith, M.D., editor, 2nd ed., pp. 741–762, 1991.

Gibson, Lewis E., M.D., et al., "A Test for Concentration of Electrolytes in Sweat in Cystic Fibrosis of the Pancreas Utilizing Pilocarpine by Iontophoresis", Pediatrics, pp. 545–549, Mar. 1959.

Brebner, D.F., et al., "The Time Course of the Decline in Sweating Produced by Wetting the Skin", J. Physiol., vol. 175, pp. 295–302, May 28, 1964.

Feldmann, Robert J., M.D., et al., "Penetration of $^{14}$C Hydrocortisone Through Normal Skin", Arch. Dermat., vol. 91, pp. 661–666, Jun. 1965.

METHOD AND APPARATUS FOR DETERMINATION OF CHEMICAL SPECIES IN BODY FLUID

This is a division of U.S. Ser. No. 08/094,787, filed Jul. 20, 1993, now U.S. Pat. No. 5,465,713, which is a continuation-in-part of U.S. Ser. No. 08/039,631, filed Mar. 30, 1993, now U.S. Pat. No. 5,438,984, which is a continuation-in-part of U.S. Ser. No. 07/989,204, filed Dec. 11, 1992, now U.S. Pat. No. 5,441,048, which is a continuation-in-part of U.S. Ser. No. 07/569,007, filed Aug. 15, 1990, now U.S. Pat. No. 5,203,327, which is a continuation-in-part of U.S. Ser. No. 07/241,707, filed Sep. 8, 1988, now U.S. Pat. No. 4,957,108.

BACKGROUND OF THE INVENTION

The present invention relates to diagnostic kits for determining the presence of one or more analytes in a fluid sample. More particularly, the present invention relates to a dermal concentration patch for increasing the concentration of an analyte expressed through the skin to a conveniently measurable level.

The determination of a patient's physiological status is frequently assisted by chemical analysis for the existence and/or concentration of predetermined chemical species in a body fluid. These tests, which are typically conducted in the physician's office or in the hospital, may be characterized by their collection technique as invasive, such as analyses of blood, or non-invasive, such as analyses of urine and perspiration.

Blood is frequently analyzed for a wide variety of components, and clinical laboratories are generally equipped with instrumentation which can provide a highly quantitative profile of the blood's composition. However, blood collection is inherently invasive, and therefore attended by several disadvantages. Analyses based upon collection of a sample of blood are generally restricted to the physician's office or clinical laboratory, which reduces convenience for ambulatory patients and greatly increases cost. In addition, some risks associated with an invasive procedure can range from undesirable at best to unacceptable, depending upon the condition of the patient, and the nature and necessity of the test desired to be performed.

Many analytes or metabolites of interest can additionally be detected in urine, which is characterized by its predictable supply and non-invasive collection. However, as will become apparent, urine analysis is not well suited for use in the principal intended application of the concentration patch of the present invention.

Perspiration is, under certain circumstances, an ideal body fluid for analysis in the determination of physiological status. Its non-invasive collection renders it suitable for use out of the physician's office, and its similarity to blood in terms of its content of biological molecules renders it suitable for a wide range of physiological testing.

Thus, a variety of diagnostic kits for monitoring an analyte in sweat have been developed. For example, U.S. Pat. No. 3,552,929 to Fields, et al. discloses a band-aid-type test patch particularly suited for determining the chloride ion concentration in perspiration as a method of diagnosing cystic fibrosis. The apparatus disclosed in Fields comprises an absorptive sweat collecting pad with an impermeable overlying layer for the purpose of preventing evaporation. When the absorptive pad is saturated, the patch is removed from the skin and exposed to a series of strips impregnated with incremental quantities of silver chromate or silver nitrate, the color of which undergoes a well known change upon conversion to the chloride salt.

U.S. Pat. No. 4,706,676 to Peck discloses a dermal collection device which comprises a binder to prevent reverse migration of an analyte, a liquid transfer medium which permits transfer of an analyte from the dermal surface to the binder, and an occlusive cover across the top of the liquid transfer medium and binder.

Peck discloses application of the dermal collection patch in the detection of human exposure to various environmental chemicals. After the dermal collection device has been worn on a patient's skin for a period of time, the patch is removed for analysis. Analysis involves chemical separation of the bound substance of interest from the binding reservoir and thereafter undertaking qualitative and/or quantitative measurement by conventional laboratory techniques.

The prior art generally suffers from one or more important limitations when convenient field use of a diagnostic test patch is desired. In particular, prior art diagnostic test patches are generally only useful for determining the presence of analytes such as halide ions, which are present in sweat in relatively high concentrations. Other prior art dermal patches are merely collection devices from which the analytes must later be separated and concentrated or otherwise prepared for analysis in accordance with known laboratory techniques. In addition, the occlusive outer layer type devices of the prior art are susceptible to the problem of back diffusion of perspiration and/or analytes contained therein.

Thus, there remains a need in many diverse applications for a method and apparatus for the non-invasive determination of a preselected analyte in a body fluid such as perspiration, which can be utilized to detect the presence of low-concentration analytes in perspiration without the need for conventional instrumentation. Additionally, these remains a need for a method and apparatus for the non-invasive determination of a preselected analyte in insensible or non-exercise perspiration. The test kit should be low-cost and suitable for convenient use by non-medical personnel.

SUMMARY OF THE INVENTION

There is provided in accordance with one aspect of the present invention a dermal concentration patch for concentrating components of a body fluid under the influence of body heat, which comprises a concentration zone in communication with a source of body fluid and a discharge zone which is exposed to the atmosphere to permit escape of at least a portion of the substantial water component and other undesired components in the body fluid.

In one embodiment, a hydrophobic membrane is provided to separate the concentration zone from the discharge zone. By hydrophobic, it is meant in the context of the present invention that the membrane prevents the passage of fluid phase but permits the escape of vapor phase of volatile components. These hydrophobic membranes shall also be referred to herein as gas permeable membranes. When a gas permeable membrane is provided, the transition of body fluid accumulated in the concentration zone to the vapor phase is accelerated under the influence of body heat, thereby concentrating the non-volatile and less volatile components in the concentration zone.

Alternatively, the concentration zone and the discharge zone may be separated by a hydrophilic layer. By hydrophilic, it is meant in the context of the present invention that the membrane or layer permits the passage of both liquid and vapor phases. Such hydrophilic layers will also be referred to herein as liquid permeable membranes. Where liquid permeable membranes are provided, passage of the fluid phase into the discharge zone is permitted.

The concentration patch is preferably provided with an analyte determination zone having detection chemistry such as an immobilized specific binding partner for an analyte to be determined in the body fluid. An analyte reference zone may additionally be provided, which provides a means for determining whether a sufficient amount of body fluid has passed through the analyte determination zone to sufficiently determine the existence of the analyte. The analyte reference zone preferably produces a visible indicium upon exposure to a predetermined threshold, such as a predetermined volume of fluid, or a threshold amount of a reference analyte such as IgG, albumin or the like.

In accordance with a further aspect of the present invention, there is provided a method of detecting false negative results in an assay of a body fluid from a subject, which are the result of noncompliance with the testing procedure by the subject. The method comprises the steps of securing a test patch to the subject in communication with a source of body fluid, the test patch comprising a first detection chemistry for detecting the presence of an analyte in the body fluid, and a second detection chemistry for detecting the presence of a reference substituent in the body fluid.

The test patch is removed from the subject after a sufficient test period of time to enable the first detection chemistry to detect the analyte, if present in the body fluid. The amount of reference substituent detected by the second detection chemistry is then determined, and the amount of reference substituent determined is compared to a predetermined value to determine whether the test patch was actually worn for substantially all of the test period.

Further features and advantages of the present invention will become apparent from the Detailed Description of Preferred Embodiments which follows, taken together with the claims and appended figures hereto.

DETAILED DESCRIPTION OF THE PREFERRED EMBODIMENTS

Figure 1:
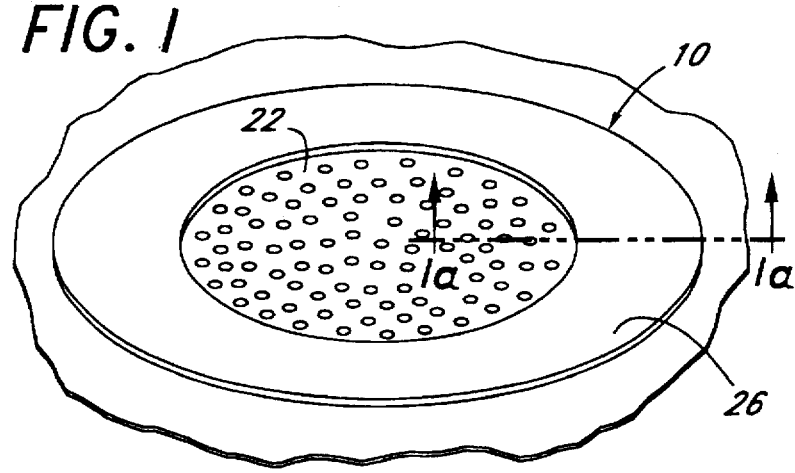
FIG. 1 is a perspective view of a dermal concentration patch according to one embodiment of the present invention.

Referring to FIG. 1, there is disclosed a dermal concentration patch 10 according to one embodiment of the present invention, illustrated as secured to the surface of the skin 12. As will be appreciated by one of skill in the art, the concentration patch of the present invention may be used for veterinary purposes as well as on humans. In addition, the concentration patch can be used in more diverse applications such as in agriculture or any other environment where a chemical species is to be detected in a fluid and a heat source such as body heat, sunlight, etc. is adaptable to effectuate the distillation or other concentration function of the patch. The preferred use, however, is for determination of preselected chemical species in sweat, and the ensuing discussion is principally directed to that end use. Moisture expressed from the skin 12 within the perimeter of the test patch 10 first accumulates in a concentration zone 14 beneath the first side of a gas permeable filter 16. The concentration zone 14 preferably contains a fluid-permeable medium 20 which may be cotton gauze or other commonly available permeable material. For example, a layer of any of a variety of known fiber webs such as knitted fabrics, or nonwoven rayon or cellulose fibers may be used. Filtration Sciences #39 is a particularly preferred fluid-permeable medium for use as a concentration zone in the present invention.

Moisture accumulates in the interfiber spaces of the medium 20 and, under the influence of body heat which is readily conducted from the surface of the skin through the fluid phase, the water component of the perspiration will tend to volatilize.

As previously discussed, the concentration patch 10 is provided with a gas permeable filter 16. By "gas permeable," I intend to designate any material which will permit the passage of the vapor phase of fluids expressed from the skin, but substantially retain the fluid phase within concentration zone 14. Any of a variety of suitable commercially available microfiltration membrane filters may be used for this purpose, such as the Gore-Tex 0.45 micron Teflon filter manufactured by W. L. Gore & Associates, Inc. (Elkton, Md.).

I use the term "liquid permeable" in this patent to mean a material which will permit the passage of sweat in the liquid phase. A liquid permeable filter will allow the passage of water in both the liquid and vapor phases. Thus, when the term "water" is used herein, I mean to refer to both the liquid and vapor phases of water, unless reference is specifically made to a particular phase.

Adjacent the second side of the gas permeable filter 16 is a discharge zone 18. As previously discussed, gas permeable filter 16 retains the fluid phase but permits escape of the vapor phase of the fluid component in perspiration. Thus, the vapor component which primarily consists of vaporized water continuously escapes through the gas permeable filter 16 exiting the second side thereof into discharge zone 18, which is in communication with the atmosphere. In an alternative embodiment, not separately illustrated, the gas permeable filter 16 is replaced by a liquid permeable membrane which permits passage of the fluid phase. In this embodiment, fluid, or a combination of vapor and fluid, will be permitted to escape from the concentration patch. Any of a variety of liquid permeable filters are commercially available which can be used to form a liquid permeable filter used in this embodiment of the present invention. A preferred liquid permeable filter is constructed from James River Paper Drape.

Disposed adjacent the second side of filter 16 in the discharge zone 18 is a flexible permeable outer layer 22. This layer serves to protect the filter 16 against physical damages such as abrasion, and can also serve as a barrier for preventing chemical contamination of the filter material from the outside. Layer 22 may comprise any of a variety of commercially available vapor permeable tapes and films which are known to one of skill in the art. Layer 22 may be distinct from or integral with tape 26 discussed below. Alternatively, depending upon the intended application of the patch, layer 22 may be deleted altogether, where it does not appear that abrasion or external contamination will deleteriously affect the concentration patch 10.

The concentration patch 10 illustrated in FIG. 1 is secured to the surface of the skin by means of a peripheral band of tape 26. Preferably, tape 26 will extend around all sides of patch 10. For example, an annular ring of tape can be die punched for use with a circular patch, or the center of a rectangular piece of tape can be removed to expose layer 22 or filter 16 of a rectangular patch. See FIGS. 1 and 3, respectively. Alternatively, layer 22 and tape 26 could be deleted altogether and layers 16 and 20 could be secured to the surface of the skin by a bandage. One such method would be to capture layers 16 and 20 under a bandage or wrapping surrounding the arm or the leg. In this case, the vapor and/or fluid is permitted to escape through 16 and 20 and into the bandage where it may either collect there or dissipate into the environment.

A large variety of hypoallergenic or other suitable tapes are well known in the art, which may be adapted for use with the concentration patch 10 of the present invention. Different tapes or adhesives may be desirable depending upon the intended use of the test kit, based upon their ability to adhere to the skin during different conditions such as daytime wearing under clothing, during sleep, during profuse sweating for prolonged periods or during showers. It has been determined that the most desirable tapes include multiple perforations which prevent sweat from building up underneath the tape and eventually compromising the integrity of the adhesive. Preferably, a tape, such as Dermiclear marketed by Johnson & Johnson, will be used.

Any of a wide variety of means for securing the concentration patch 10 to the skin 12 may be utilized. For example, the tape 26 can be eliminated and gauze layer 20 provided with a lower adhesive layer to perform the same function. One such adhesive membrane is the MN-100 adhesive membrane manufactured by Memtec of Minnetonka, Minn. This membrane is liquid permeable so that it passes fluid as would the gauze layer 20, yet has one adhesive side so that it will stick to the skin. Alternatively, outer protective layer 22 can comprise an annular flange 23, extending radially outwardly beyond the outer edges of filter 16 and gauze 20. See FIG. 2a. The lower surface of the flange 23 is then provided with a suitable adhesive.

The surface temperature of human skin varies regionally, however, it is generally within the range of from about 86° to about 90° F. at rest, and can rise to much higher temperatures under conditions of strenuous exertion. At those temperatures, a number of chemical species of interest for the purpose of the present invention, such as creatine kinase, a high or low density lipoprotein have a sufficiently low vapor pressure that volatilization is not a significant factor in the efficiency of the concentration function. At the same time, the substantial aqueous component will have a sufficiently high vapor pressure that it will tend to volatilize thereby concentrating the less volatile fractions. However, in some applications, the chemical species of interest will have a high enough vapor pressure, even at the resting temperature, such that escape of the vapor phase through the gas permeable filter 16 of the analyte of interest will disadvantageously impair the efficacy of the test patch. For these analytes, a modified concentration patch must be used.

Figure 2:
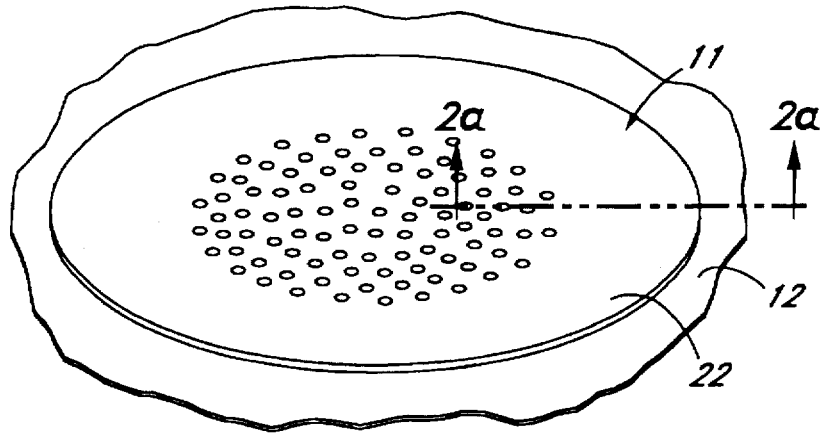
FIG. 2 is a perspective view of a dermal concentration patch according to a second embodiment of the present invention.
Figure 2A:
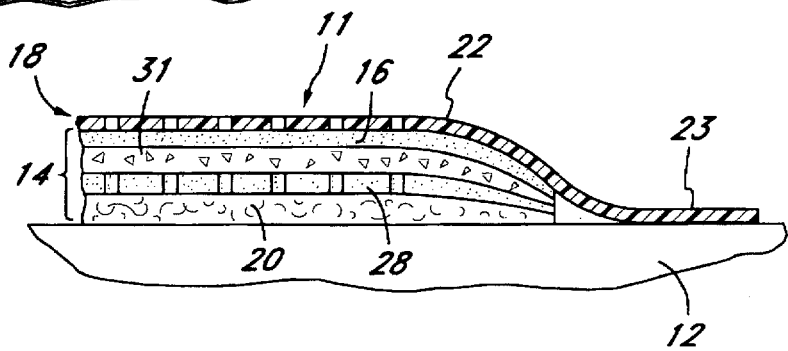
FIG. 2a is a cross-sectional view along line 2a—2a of the dermal concentration patch of FIG. 2.

Referring to FIGS. 2 and 2a, there is disclosed a modified concentration patch 11 according to the present invention for use with an analyte having a propensity to escape through the gas permeable filter 16 as a vapor under ordinary use conditions. The test patch comprises a concentration zone 14 defined on its inner boundary by the skin 12 to which the concentration patch 11 is secured. The outer boundary of the concentration zone 14 is defined by gas permeable filter 16, which separates the concentration zone 14 from the discharge zone 18. Disposed in the concentration zone 14, and adjacent the gas permeable filter 16, is a binder layer 30 for binding and preventing the escape of molecules of the volatile analyte. The binder layer 30 is separated from the gauze layer 20 by a porous layer 28, which may compromise any of a variety of films for retaining the binder layer 30 yet permitting passage of fluid.

In the embodiment illustrated in FIG. 2a, perspiration will pool in the interfiber spaces of the gauze 20, and will percolate through porous layer 28 into the binder layer 30. In that layer, a chemically active or biochemically active binder material will act to selectively bind the volatile analyte, thereby preventing it from escaping as a vapor through gas permeable filter 16. As discussed in connection with the embodiment illustrated in FIG. 1, it is also possible to replace the gas permeable filter 16 with a liquid permeable layer, where the presence of fluid on the outside of the test patch would not be undesirable.

The binder layer 30 may comprise any of a variety of binders depending upon the nature of the volatile analyte to be determined. For example, the binder may chemically bind with the analyte or adsorb the analyte to be determined. In addition, the binder layer may comprise a specific binding partner of the analyte to be determined, such as a polyclonal or monoclonal antibody or an antigen matched to a specific antibody desired to be measured in the perspiration.

The concentration patch 11 is additionally provided with tape 26 or another means for securing the patch to the skin of a subject, as has been detailed in connection with the embodiment illustrated in FIG. 1. Concentration patch 11 is illustrated, however, as having a unitary outer layer 22 extending beyond the perimeter of the underlying layers to form an annular flange 23, which is provided with an adhesive on its lower surface. As discussed in connection with the embodiment of FIG. 1, outer protective layer 22 permits the escape of water vapor yet protects the material from chemical contamination from the outside.

Figure 3:
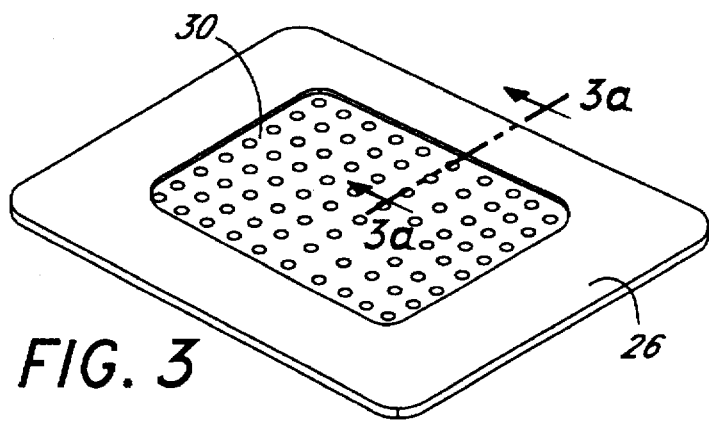
FIG. 3 is a perspective view of a third embodiment of the dermal concentration patch of the present invention.
Figure 3A:
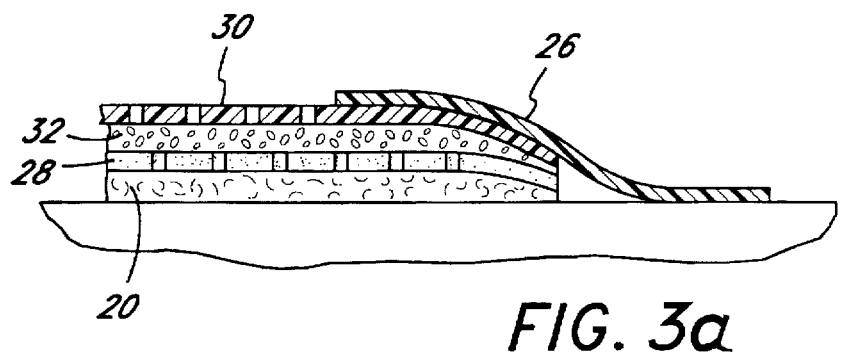
FIG. 3a is a cross-sectional view along the line 3a—3a of the patch of FIG. 3.

Referring to FIGS. 3 and 3a, there is disclosed a further embodiment of the test patch of the present invention wherein an inner porous layer 28 and an outer porous layer 30 define a space for containing a microbead layer 32. The inner layer 28 and outer layer 30 preferably comprise the same material, which may be any suitable material for providing an unrestricted flow of fluid through the patch while trapping the microbeads in between. One suitable material for porous layers 28, 30 is the liquid permeable and microporous film known by the name Ultipor (nylon 6) and manufactured by Pall Corporation in Glen Cove, N.Y. Additional manufacturers of suitable nylon filtration membranes include Micron Separations, Inc. of Westborough, Mass., and Cuno of Meridan, Conn. Porous layers 28, 30 may also be comprised of materials other than nylon, such as polycarbonate, modified polyvinylchloride and polysulphone.

The gauze, the inner and outer porous layers and the adhesive tape in all embodiments could be cut to size with conventional dies. The gauze 20 and the inner porous layer 28 could be fixed to the adhesive ring 26 with conventional adhesives, such as used on the adhesive surface itself. Alternatively, they could be heat or ultrasonically bonded together. The proper amount of microbeads could then be placed on top of the inner porous layer and then the outer porous surface attached by similar means. Typically, in a one-inch diameter patch, from about 0.05 grams to about 1 gram of microbeads will be used, and preferably from about 0.1 to about 0.4 grams will be used. The inner and outer porous surfaces may have to be staked or spot-welded together in some pattern, as will be appreciated by one of skill in the art to prevent the microbeads from collecting in one area.

The free adhesive surface optionally is covered by pull-away paper (not illustrated) with adequate space to be gripped with one's fingers. The patch is packaged in a paper or plastic pouch similar to that used in conventional band-aid packaging. The assembled unit could be terminally sterilized or pasteurized prior to sale. Alternatively, the package could comprise a vapor barrier such as a metallic foil or mylar and even include oxygen or moisture absorbent means such as a small packet of any of a variety of known desiccants, such as silica gel, calcium chloride, calcium carbonate, phosphorous pentoxide or others as will be appreciated by one of skill in the art.

The total thickness of microbead layer 32 can be varied considerably. However, if the color change is to be developed by immersion of the patch in appropriate reagent baths, layer 32 is preferably no more than about 3 mm thick since color changes occurring at immobilized sites on thicker layers would not likely be observable. More preferably, the microbead layer is between about 1 mm and about 2 mm thick. Alternatively, microbead layer 32 could be torn open, releasing loose microbeads which could be used to conduct chemical analysis for presence of the unknown by conventional means, such as in a cuvette.

Optimally, the diameter of the beads in microbead layer 32 will be at least about one order of magnitude larger than the diameter of the pores in inner porous layer 28 and outer porous layer 30. For example, the beads contained in microbead layer 32 may have diameters within the range of from about 5 to 50 microns, and preferably within the range of from about 5 to about 10 microns. If 10-micron diameter beads are utilized in the microbead layer 32, for example, inner porous layer 28 and outer porous layer 30 will optimally comprise a median pore size of approximately 1 micron.

Microbead layer 32 may comprise any of a variety of known materials including polystyrene, latex and glass. Beads sized from approximately 0.05 micron to 100 micron which are suitable for the present application are available from Polysciences of Warrington, Pa.

Microbead layer 32 serves as the support for an immobilized specific binding partner for the analyte to be determined. Thus, a molecule with a high chemical affinity for a specific component in the fluid to be analyzed will be immobilized to the microbeads in microbead layer 32.

Figure 5:
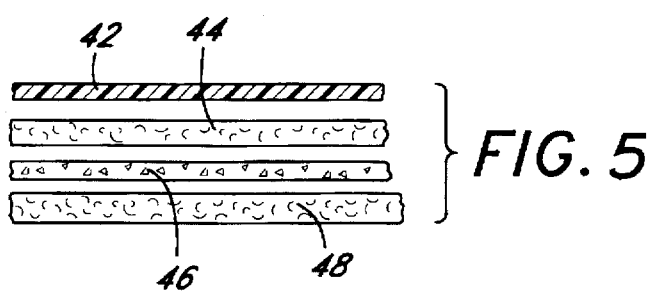
FIG. 5 is an exploded elevational schematic view of a fourth embodiment of the present invention.

Referring to FIG. 5, there is disclosed a further embodiment of the present invention, particularly suited for use under conditions in which profuse sweating is not present, such as in passive insensible perspiration, wherein the test patch is provided with an impermeable outer layer 42. In order to minimize any back diffusion of fluid into the skin, an absorptive layer 44 is provided to form a reservoir for drawing moisture away from the surface of the skin and through support 46 to which is bound a specific binding partner for at least one analyte to be determined. Layer 44 may include chemical means for binding or collecting moisture such as a desiccant as has been previously discussed, which is suitable for use in proximity to the skin. The patch may be further provided with an underlying porous layer 48 to separate support 46 from the surface of the skin, and the patch is provided with any of the means for attachment to the skin as have been previously discussed.

In one preferred embodiment of the present invention, the analyte to be determined in perspiration is the enzyme creatine kinase MB (CK-MB) which is expressed from the cardiac muscle during myocardial infarction and other cardiac distress. A monoclonal antibody raised against CK-MB can be immobilized to the microbeads in accordance with any of a variety of conventional methods, such as the cyanogen bromide technique described in Pharmacia product literature (Pharmacia, Inc., Piscataway, N.J.).

The monoclonal antibodies useful in the present invention may be produced and isolated by processes which are well known in the art, such as those discussed by Milstein and Kohler, reported in *Nature*, Vol. 256 at 495–497 (1975). In particular, Jackson describes a method of producing anti-CK-MM (an indicator of the status of skeletal muscles) and anti-CK-MB antibodies in *Clin. Chem.*, 30/7, 1157–1162 (1984).

In accordance with one known process, mice such as Balb/c female mice or other mouse strains or even other suitable animals such as rats or rabbits are immunized with an amount of the CK-MB enzyme to initiate an immune response. The enzyme dosage and immunization schedule for producing useful quantities of suitable splenocytes can be readily determined depending on the animal strain used.

The size and spacing of doses of CK-MB or other antigen are of prime importance in the antibody response. Fortunately, a wide range of antigen doses commonly affords immunity against harmful agents. Thus, a small dose of antigen is usually sufficient to initiate an antibody response, i.e., microgram quantities of proteins are frequently adequate. However, a minimum dosage for initiating an immune response does typically exist, although doses of antigen below the minimum dose necessary to initiate an antibody response will usually maintain antibody production which is already in process. For example, an initial immunization with approximately 50 μg of the enzyme may be followed by a hyperimmunization series of five injections.

When certain compounds which are themselves not necessarily antigenic are mixed with an antigen, enhanced antibody production against the antigen occurs, as evidenced by the appearance of large amounts of antibody in the serum, a prolonged period of antibody production, and a response to lower doses of antigen. Such substances are called "adjuvants" and include Freund's incomplete and complete adjuvants and alum gels. Thus, a given dose of antigen is usually more effective when injected subcutaneously with an adjuvant or when injected as repeated small aliquots than when administered intravenously.

Typically, the adjuvants of Freund are preferred. The original "complete" Freund's adjuvant mixture consists of mineral oil, waxes and killed tubercle bacilli. Antigen is added to the adjuvant mixture in an aqueous phase to form a water-in-oil emulsion in which each water droplet is surrounded by a continuous oil phase containing tubercle bacilli. The mixture is commonly injected subcutaneously into experimental animals. Injection stimulates a marked granulomatous reaction with lesions consisting largely of collections of histiocytes, epithelioid cells and lymphocytes. The local lymph node shows a small increase in plasma cells.

Following the immunization with a primary dose of a soluble protein antigen, specific antibodies normally first appear in the serum after a few days increase until about the second week, and thereafter, slowly decline over a period of weeks to months.

The first serum antibodies to appear after antigenization are IgM antibodies. These are usually followed by the appearance of IgG antibodies. Later, as antibody serum levels increase, IgM antibodies disappear, probably as a result of specific feedback suppression of IgG antibodies.

After the "primary response" to a protein has passed, a second dose of the same antigen given months or even years later usually elicits an intense and accelerated "specific secondary response" in which serum antibody usually begins to rise within two or three days of exposure. The serum levels of antibody in a secondary response may reach as high as 10 mg per ml.

The animal is subsequently sacrificed and cells taken from its spleen are suspended in an appropriate medium and fused with myeloma cells, such as those obtainable from the murine cell line Sp2/0-Ag14. The result is hybrid cells, referred to as "hybridomas," which are capable of reproduction in vitro and which produce a mixture of antibody specific to each of the various recognizable sites on the CK-MB enzyme.

The myeloma cell line selected should be compatible with the spleen cells, and optimally of the same species. Although the murine cell line Sp2/0-Ag14 has been found to be effective for use with mouse spleen cells, other myeloma cell lines could alternatively be used. See, for example, *Nature*, Vol. 276 at pp. 269–270 (1978).

The myeloma cell line used should preferably be of the so-called "drug resistant" type, so that any unfused myeloma cells will not survive in a selective medium, while hybrid cells will survive. A variety of drug resistant myelomas are known.

The mixture of unfused spleen cells, unfused myeloma cells and fused cells are diluted and cultured in a selective medium which will not support the growth of the unfused myeloma cells for a time sufficient to allow death of all unfused cells. A drug resistant unfused myeloma cell line will not survive more than a few days in a selective medium such as HAT (hypoxanthine, aminopterin and thymidine). Hence, the unfused myeloma cells perish. Since the unfused spleen cells are nonmalignant, they have only a finite number of generations until they fail to reproduce. The fused cells, on the other hand, continue to reproduce because they possess the malignant quality contributed by the myeloma parent and the enzyme necessary to survive in the selected medium contributed by the spleen cell parent.

The supernatant from each of a plurality of hybridoma containing wells is evaluated for the presence of antibody to a specific site unique to the CK-MB enzyme structure. Hybridomas are then selected producing the desired antibody to that specific site. This selection may be, for example, by limiting dilution, in which the volume of diluent is statistically calculated to isolate a certain number of cells (e.g., 1 to 4) in each separate well of a microliter plate. In this way, individual hybridomas may be isolated for further cloning.

Once the desired hybridoma has been selected, it can be injected into host animals of the same species as those used to prepare the hybridoma, preferably syngeneic or semi-syngeneic animals. Injection of the hybridoma will result in the formation of antibody producing tumors in the host after a suitable incubation time, resulting in a very high concentration of the desired antibody in the blood stream and in the peritoneal exudate of the host. Although the hosts have normal antibodies in their blood and exudate, the concentration of these normal antibodies is only about 5% of the concentration of the desired monoclonal antibody. The monoclonal antibody may then be isolated in accordance with techniques known in the art.

Alternatively to raising anti-CK-MM monoclonals as described, the components of a commercially available diagnostic kit could be utilized, which incorporates the CK-MM enzyme chemically bound to a bead support. A suitable kit marketed as the Isomune-Ck Diagnostic Kit by Roche of Nutley, N.J., is one commercially available candidate. This kit includes a goat antisera to human CK-MM and donkey anti-goat antibody covalently bound to styrene beads. A mixture would produce an immobilized conjugate having a specific affinity for human CK-MM. A more direct and less expensive procedure, however, would be to immobilize the anti-CK-MM monoclonal antibody directly to the microbead support in accordance with methods now well known in the art.

The antibody which is to be used for purpose of complexing with CK-MB may be immobilized on any of a variety of supports known in the art. For example, anti-CK-MB antibody may be bound to polysaccharide polymers using the process described in U.S. Pat. No. 3,645,852. Alternatively, the antibody may be bound to supports comprising filter paper, or plastic beads made from polyethylene, polystyrene, polypropylene or other suitable material as desired. Optimally, the support will take the form of a multiplicity of microbeads which can conveniently be formed into microbead layer 32, illustrated in FIG. 3a.

Figure 1A:
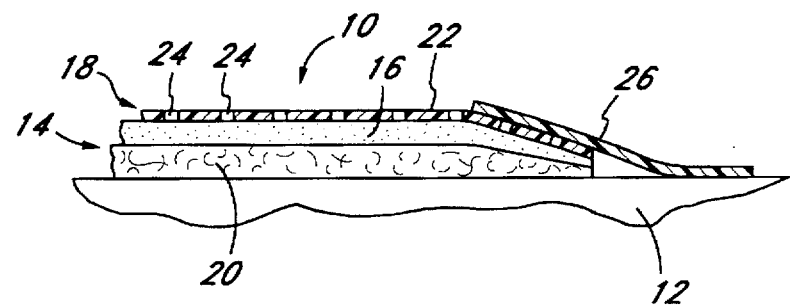
FIG. 1a is a cross-sectional view along the line 1a—1a of the dermal concentration patch of FIG. 1.

As an alternative to a microbead support layer, the specific binding partner could be immobilized directly to the inner porous layer 20 or 28 on FIG. 3a or to the underside of filter 16 of FIG. 1a. In this manner, the need for microbead layer 32 could be eliminated entirely. Liquid permeable membranes which are specifically designed for binding antibody proteins are commercially available, such as Zetapor from Cuno, and Protrans, available from ICN in Costa Mesa, Calif.

Figure 4:
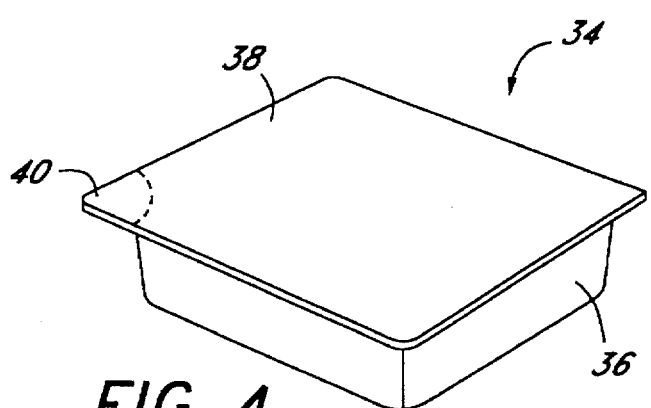
FIG. 4 is a perspective view of one embodiment of a reagent packet for use in effecting a color change responsive to the presence of analyte in the concentration patch of the present invention.

Referring to FIG. 4, there is disclosed a reagent packet for use with the concentration kit of the present invention. The reagent packet 34 comprises a container 36 having a removably secured top 38. A flap 40 on the top 38 facilitates gripping the top 38 and peeling away from container 36 to reveal the reagent contained therein.

Typically, after the test patch has been worn for a suitable period of time, it will be removed by the wearer (in non-drug screen tests) and developed to produce a visible indicium of the test result. The test patch can be marketed together with a developer packet such as packet 34 which contains known developer reagents for the immunoassay. For example, a protein electrophoresis stain such as Coomassie brilliant blue or amido black 10b, can be bound to purified analyte contained in the reagent packet 34. When a test patch is immersed in the packet 34, any antibodies on the test patch that are unbound by analyte in the perspiration will become occupied by stained purified analyte in the packet 34. There will thus be an inverse relationship between the amount of stain absorbed by the patch and the amount of enzyme passed through the patch. In this embodiment, the user would place the patch in the fluid of the packet 34, wait for some period of time such as 30 seconds or more, rinse the patch under tap water and relate the resultant color of the patch to the presence of the enzyme. A color comparison chart and control zone on the patch having no bound antibody may be provided to aid in this interpretation.

Alternatively, the user could support the test patch on an open vessel, such as a small jar or vial, or empty container similar in design to reagent packet 34 securing the adhesive border of the patch to the rim of the vessel, and then pour contents of packet 34 on top of the test patch. Gravity would assist the transport of the contents of packet 34 through the test patch to maximize the efficiency of the stain/binding reaction, and to facilitate visualization of the color change.

The system could readily be designed so that the user performs the interpretation of the concentration of the analyte not in the patch at all but by observing the packet contents once the contents have traversed the patch. This method would be similar to conventional ELISA assay methods where the packet contents contain enzyme conjugates which will react to specific enzyme substrates. The enzyme substrates would be added to the packet contents after those contents transversed the test patch.

If the perspiration contained molecules of interest, they would bind to the specific immobilized binding partner on the patch. If this occurred, enzyme conjugates in the packet would pass freely across the test patch and enzymatically modify the enzyme substrate producing a controlled color change in the solution in the packet. If the perspiration contained the desired molecules of interest, enzyme conjugates would then be bound in transit across the patch and would be unavailable to cause color change in the substrate solution. Other immunoassay schemes can be readily adapted for use in the present invention by one of skill in the art.

Although the concentration patch of the present invention could be used for any of a variety of body fluids, perspiration is the desired fluid due to its dependable supply and its similarity to blood, albeit with lower analyte concentrations. Saliva also appears to contain many of the chemical components of blood, however, often at even lesser concentrations than found in sweat.

In performing the method of the present invention, the concentration patch may advantageously be located on different regions of the body depending upon a variety of factors. It is well known that the quantity of perspiration generated is a function of both the location on the body, as well as the physical activity during and immediately preceding collection. This is due to both different densities of sweat glands on different regions of the body, as well as to certain regulatory functions of those glands.

Sweat glands are classified to be either of two types. Eccrine type function primarily to regulate body temperature through their relationship to evaporative heat loss. It is the eccrine type sweat gland that provides the sweat associated with exercise and is therefore the source of perspiration of interest for many applications of the concentration patch of the present invention. Apocrine type sweat glands are larger secreting elements which are localized only in relatively isolated areas of the body such as the axilla, pubic and mammary areas.

Although the etiology of perspiration is relatively complex, it is known to be caused by both mental states such as mental exercise and emotional distress; thermal stress, as the sedentary body's response to temperature control; and exercise stress as the physically active body's response to temperature control.

In addition to the foregoing distinctions, perspiration can be either insensible or sensible. Insensible sweat appears to be caused by water diffusion through dermal and epidermal layers. Its purpose appears to be not related to thermal regulation at all, but to aid in such things as the improvement of mechanical interaction between the skin and surfaces to facilitate grip. Further complexities arise with regard to the spatial distribution of sweat glands and the flow rates of the various types of perspiration. Specialized areas of the palms and soles of the feet sweat continuously, although at a very low rate. The rate of insensible perspiration is dependent upon the position of the particular area in question relative to the heart. For example, elevating a limb over the heart decreases the insensible perspiration rate.

At temperatures of less than about 31° C. in a resting human adult, insensible perspiration proceeds at a rate of between about 6–10 grams per square meter per hour from the skin of the arm, leg and trunk, up to about 100 grams per square meter per hour for palmer, planter and facial skin. The latter three areas jointly account for approximately 42% of the total water loss from the body under non-sweating conditions, which generally means an air temperature of between about 24°–26° C. Such insensible perspiration first begins on the dorsal surfaces of the foot and spreads to higher places on the body as the temperature increases. One reported study determined that the average water loss due to insensible perspiration for a body surface area of 1.75 square meters ranged from 381 ml, 526 ml and 695 ml per day at ambient temperatures of 22° C., 27° C. and 30° C., respectively.

In contrast to insensible perspiration which does not appear to be associated with a particular surface element of the skin, sensible perspiration has been associated with the eccrine gland. The number of actively secreting eccrine glands varies among individuals and depends upon the part of the body observed and the type of sweat response created. Maximum gland density varies from between about 200 per square centimeter on the forearm to over 400 per square centimeter on the thenar eminence.

The appearance of sensible sweat begins at either when the skin temperature exceeds about 94° F. or the rectal temperature exceeds about 0.2° F. over normal core temperature. Maximum rates of sweat volume loss can be as high as 2 liters per hour in average subjects and can be as high as 4 liters per hour for brief periods. Sensible perspiration begins in the distal parts of the lower extremities and progresses upward as the environmental temperature is elevated. Thus, the dorsum of the foot begins to sweat long before the chest. The pattern of sensible sweat response also shifts from one region of the body to another as the thermal stress increases. Under mild thermal stress, sweating is present mainly in the lower extremities. As the thermal stress further increases, sweating spreads to the trunk. Due to its large surface area, the trunk becomes the dominant water loss surface. Eventually, extremely high rates are found in the trunk while rates in the lower extremities may actually decline. The forehead can produce extremely high sweat rates but is among the last areas to sweat in response to thermal stress.

As has been described previously, a large variety of chemical species which are detectable in blood are also present in sweat, although typically in a much lesser concentration. Early investigation into the composition centered on electrolytes, including sodium, chloride, calcium and potassium. Extreme individual variation was found among individuals, and the electrolyte composition also differed depending upon whether the sweat was stimulated by thermal, mental or other etiology.

Further research has identified numerous additional components in sweat, including both electrolytes and more complex biological molecules. Some illustrative chemical species which have been identified in sweat are identified in Table I below.

TABLE I

Chemical Components of Sweat

| | |
|---|---|
| diphtheria antitoxin | sulfates |
| ascorbic acid | iodine |
| thiamine | iron |
| riboflavin | fluorine |
| nicotinic acid | bromine |
| amino acids | bismuth |
| ethanol | lactic acid |
| antipyrine | pyruvate glucose |
| creatinine | nitrogen |
| C-14 methylurea | ammonia |
| C-14 acetamide | uric acid |
| C-14 urea | nicotine |
| thiourea | morphine |
| paraaminohippuric acid | sulfanilamide |
| mannitol sucrose | atabrin |
| lactate | methadone |
| sodium chloride | phencyclidine |
| potassium | aminopyrine |
| calcium | sulfaguanidine |
| magnesium | sulfadiacine |
| phosphorous | amphetamines |
| manganese | benzoylecgonine |
| theophylline | phenobarbital |
| parathion | androgen steroids |
| tetrahydrocannabinol | phencyclidine |
| insulin | phenytoin |
| cimetidine | carbamazepine |
| dimethylacetamide | |

Any of the entries in Table I for which affinity chemistry can be developed, can be an appropriate subject of a test patch according to the present invention. Since most of the components listed in Table I are non-volatile, they will be trapped in the concentration zone 14 of the concentration patch 10 illustrated in FIG. 1a, or on the binder layer 30 of FIG. 6. However, some components, most notably ethanol, would volatilize under the influence of body heat thereby enabling escape in the vapor phase through the test patch. Where the analyte to be determined is ethanol or another volatile component, the concentration patch of the present invention may be modified as described in connection with the embodiment illustrated in FIG. 2.

Figure 6:
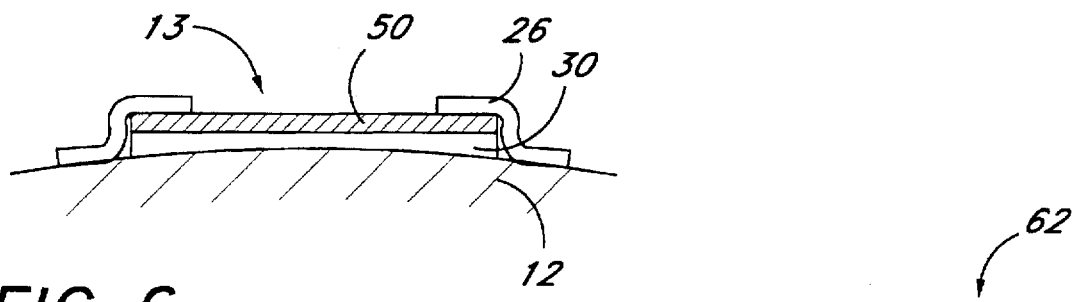
FIG. 6 is a cross-sectional view of a dermal patch according to a further embodiment of the present invention.

Referring to FIG. 6, there is disclosed a modified concentration patch 13 according to the present invention, in which all intervening layers between the skin 12 and the binder layer 30 have been deleted. By disposing the binder layer (i.e., the layer having a specific binding partner for an analyte to be determined) directly adjacent the skin, lateral diffusion of sweat throughout the binder layer 30 is minimized. The proximity of the binder layer 30 to the skin 12 allows the output of each duct of the sweat glands to contact or be in fluid communication with a relatively small area of the binder layer 30. For a variety of reasons which will be apparent to one of skill in the art, it may also be desired to mount a microporous membrane, preferably a liquid permeable membrane 50 atop the binder layer 30.

The evaporative capacity of the binder layer 30 and the liquid permeable membrane 50 is preferably sufficient relative to the output capacity of the individual sweat ducts, to minimize lateral diffusion of sweat away from the immediate area the duct. This embodiment has special application for monitoring the chemical composition of insensible perspiration and/or non-exercise perspiration, in instances where output from the sweat glands is limited. Due to the magnification effect detailed infra, the present embodiment is also particularly suited for monitoring low concentration analytes.

By limiting the suppressive characteristics of moisture or water on the skin, through the use of materials having a maximal evaporative capacity, the instant embodiment allows increase of the through-put rate of sweat in the patch by maximizing sweat gland output. Nadel and Stolwijk (*J. Applied Physiology*, 1973, 35(5); 689–694) disclose that sweat gland activity is suppressed by water lying on the skin, finding a difference in whole body sweat rate of 40% between wet and dry skin. Mitchell and Hamilton (*Biological Chemistry*, 1948, 178:345–361), found that loss of water and solutes in insensible perspiration presumably stops whenever the surface of the skin is covered with a film of water. Brebner and Kerslake (*J. Physiology*, 1964, 175:295–302) postulate that the reason for this phenomenon is that water in contact with the skin causes the epidermal cells of the skin to swell and thus block the sweat ducts.

The ability of the present invention to produce a positive response based upon the presence of relatively low concentrations of analyte is particularly advantageous in view of the fact that, during active exercise, a ¼" diameter area of skin provides approximately 35 microliters of sweat per hour, whereas a similar diameter area of skin produces sweat at a non-exercise rate of only about 3.2 microliters per hour. The present embodiment is further advantageous as not requiring the user to exercise, but only to wear the patch for an equal or typically longer period during rest or at normal activity levels.

Thus, homogeneous diffusion of sweat throughout the binder layer is preferably minimized when using the instant invention in conjunction with insensible and/or non-exercise perspiration and/or a determination of minute amounts of analyte contained within perspiration. The minimized lateral diffusion of perspiration throughout the binder layer 30, according to the present invention, provides a more concentrated collection of sweat at each sweat duct, thereby providing a greater amount of selected analyte to be determined at that area.

Sato and Fusako (*American J. Physiology*, 1983, 245(2): 203–208) estimate that the diameter of the duct of the sweat gland is approximately 40 microns. According to Scheupoein and Blank (*Physiological Review*, 1971, 51(4): 702–747), the average density of sweat glands on the skin surface is approximately 250 per square centimeter. Thus, the total surface area of sweat gland ducts of the skin represent 1/318 of the total surface area of the patch of the instant invention. The visible result on a test patch of the present invention when, for example, using known ELISA technology to determine a low concentration analyte, is the appearance of a number of tiny color changes on the binder layer 30 associated with the output of specific ducts. If significant lateral diffusion of sweat is permitted prior to contact with the immobilized binding partner, the color change is frequently too diffuse to detect with the naked eye.

Although a patch incorporating the present embodiment of the invention may be worn at any practical location on the body, preferable locations for the patch include the skin on the sole of the foot, and areas on the chest and back. The patch is able to be worn in confidence in these areas, and these areas are not covered with excessive hair, so that the patch may be secured with conventional adhesive tapes.

Hertzman et al. (*J. Applied Physiology*, 1952(5): 153–161) determined that the rate of sweat output from the sole is independent of environmental temperature, and, from this, it is suspected that it is also independent of activity level. Therefore, as the sole does not generate exercise sweat, the input to a patch on this location would be independent of the activity level of the wearer.

Figure 7:
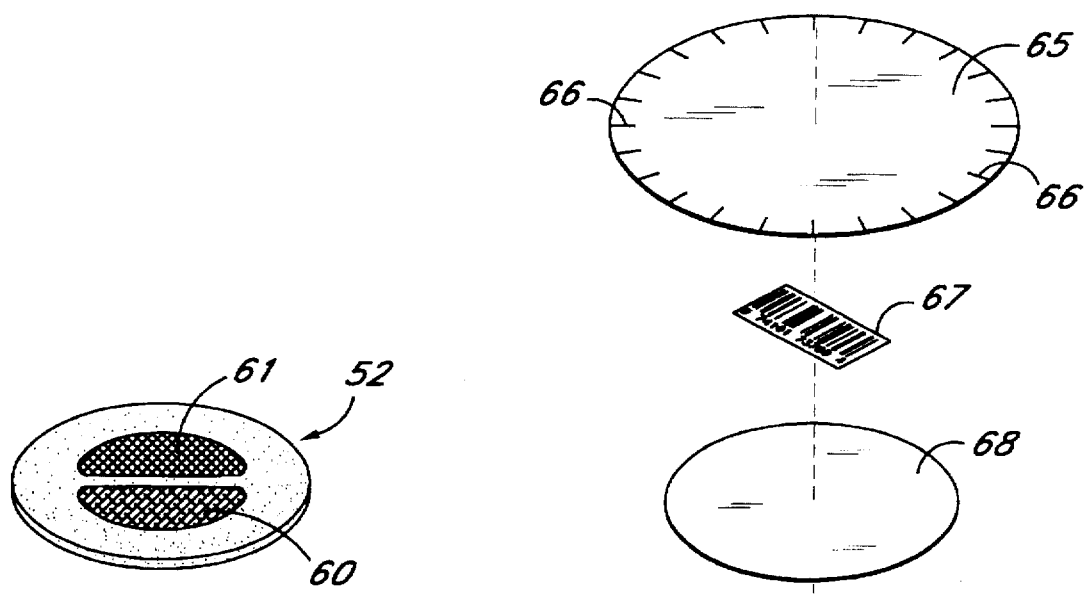
FIG. 7 is a plan view of a dermal patch according to another embodiment of the present invention.

Referring to FIG. 7, there is shown a modified binder layer 52 for a concentration patch according to the present invention, wherein two or more distinct zones are provided on the binder layer 52. The use of a reference zone or of several distinct test zones is contemplated for both the single layer patch discussed in connection with FIG. 6, as well as the embodiments discussed in connection with FIGS. 1–3a and 5. The multi-zone binder layer 52 may also be used for certain embodiments to be discussed hereinafter in connection with FIGS. 6–10 when specific binding chemistry is used.

One or more of the zones, such as determination zone 60 (FIG. 7), is used to test for an analyte of interest within the sweat, as detailed previously. One or more of the remaining zones, such as reference zone 61, is used as a reference indicator.

Reference zone 61 performs a variety of functions, depending upon the desired application of the test patch. For example, reference zone 61 can be provided with color change chemistry as discussed previously to provide the wearer with an indication that the patch has been worn for long enough that a sufficient sample volume has traversed the patch to provide a meaningful test for the analyte of choice. For this purpose, reference zone 61 is provided with affinity chemistry for a preselected reference substituent such as IgG, albumin or any other sweat component which is reliably present. Preferably, the selected reference substituent is one which provides a reasonably accurate measurement of the volume sweat put through the system.

This use of the reference zone 61 may be facilitated by first determining the rough concentration ratio of a reference substituent such as albumin to the analyte to be determined and providing the patch with color change chemistry which provides a visual indication of the presence of the reference substituent only well after the elution of the analyte to be determined has exceeded the lower limits of detection.

Reference substituents such as albumin will typically be present in significantly greater quantities than the analyte. Thus, in order to accomplish the objective of indicating passage of a sufficient sample volume, the "sensitivity" of the patch for the reference substituent is preferably lower than for the analyte. This can be achieved by using a proportionately lower amount of specific binding partner for the reference substituent than for the analyte, other dilutions in the assay, or simply selecting a less abundant reference substituent. Selection of a suitable reference substituent and concentration determinations can be readily made through simple experimentation by one of skill in the art.

Alternatively, and particularly useful in assays for drugs of abuse and their metabolites, a reference zone 61 can provide an indication that the skin patch was actually worn by the desired patient, parolee or other subject. One inherent limitation in a test in which a subject desires a negative result is the possibility that the subject will simply remove the patch after administration and replace it just prior to reexamination. This possibility gives rise to the ability of the wearer to ensure false negative results.

However, by provision of a reference zone 61 to detect a known component in sweat, the test results will reveal test patches that have not been worn for the test period. Reference zone 61 thus provides a method of preventing false negative evaluations due to tampering or removal of the test patch.

A reference zone 61 to detect a known component in sweat may also be provided as a positive control zone to ensure the discovery of false negative test results due to degradation of reagents or other components of the patch.

In non drug-of-abuse screens, the indication produced within the reference zone 61 will preferably be a visible color change by a chemical or antibody/antigen colorimetric interaction occurring or becoming apparent to the wearer when a predetermined amount of the reference analyte has passed through the interaction area.

Optionally, a reference zone 61 may be provided as a negative control zone to enable the discovery of false positive results. A preferred negative control zone will have an immobilized specific binding partner for an analyte known to be absent in human sweat. The analyte's specific binding partner must be known to not cross react with components present in human sweat. An example of an appropriate analyte is bacteriophage T4 coat protein.

In yet a further embodiment of the present invention (not illustrated) two or more analyte determination zones 60 are provided in a single test patch. The use of multiple test zones is particularly useful in applications such as a drug of abuse screen where testing for any one or more of a wide variety of analytes may be desired. For example, a single test patch may be used to screen for any of a plurality of drugs of abuse, such as THC, Phencyclidine morphine and Methadone. A positive result for any of the drugs on the screen may provide sufficient proof of an offense such as a violation of parole, or can be used to signal the need for more quantitative follow up investigations. Used as an initial screening tool, the present invention offers the advantages of being non-invasive, and much less expensive than conventional quantitative analyses. For these reasons a screening test patch as disclosed herein is particularly suited for initial screening of large populations such as parolees, inmates, military personnel or others where monitoring is desired.

The analyte determination zone 60 and analyte reference zone 61 may be physically separated on the patch, such as in concentric circles or discrete zones, as illustrated in FIG. 7, or in the case of only two or three analytes, interspersed throughout. In the latter case, positive results of different determinations would be indicated by the appearance of different colors.

A variety of well known immunoassay schemes for visualizing the presence of an analyte of interest are well known in the art, and need not be detailed here. However, the optimal immunoassay scheme is generally one which is simple and requires the fewest steps. For many types of assays, it will be desirable for the wearer to obtain rapid results such as a color change to demonstrate a positive or negative result with as few steps as possible. On the other hand, drug of abuse screens are more likely to be evaluated by clinical staff instead of by the test subject, and there is less concern for a "user friendly" product.

For example, in a concentration patch of the present invention designed for determining both the presence of CK-MM and CK-MB enzyme, the immobilized specific binding partner for each of those enzymes will be segregated to separate regions of the test patch. In this manner, if an enzyme-linked immunoassay system is utilized, a common enzyme and a common substrate could be used. Alternatively, a different color is used to express the presence of different analytes.

Figure 8:
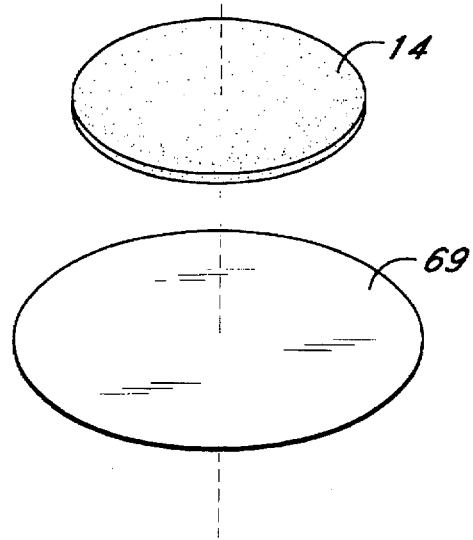
FIG. 8 is an exploded elevational view of a dermal concentration patch according to yet another embodiment of the present invention.

Another embodiment of the present invention which will indicate whether a wearer has removed the patch during the examination period is illustrated in FIG. 8. In this embodiment, the concentration patch 62 is secured to the skin 64 with an adhesive member 65. The adhesive member 65 is preferably constructed of a material that is strong enough to hold the concentration patch 62 to the skin 64, but that is relatively easily torn such as during removal of the patch from the skin. A suitable material for use in this preferred embodiment is Tegaderm 1625, manufactured by Minnesota, Mining, and Manufacturing Corp. of St. Paul, Minn. Other companies, including Avery and Johnson & Johnson, manufacture similar suitable materials; the Johnson & Johnson product being sold under the trademark "Bioclusive." It has been found, however, that with sufficient patience, a wearer could remove an adhesive member of this type and replace it without leaving any visible indication that the adhesive member has been removed. Therefore, in the particularly preferred embodiment shown, the adhesive member 65 has stress razors 66 in the form of a plurality of radial slits around its outer perimeter. The stress razors 66 can be arranged in any of a wide variety of configurations and densities and accrue the advantage of tearing upon removal, as will be apparent to one of skill in the art.

In the preferred embodiment illustrated in FIG. 8, the radial slits 66 extend approximately 0.05 inches in length from the outer edge toward the center of the concentration patch 62. The slits 66 may be arranged with any of a variety of regular or irregular spacings therebetween, and, in the preferred embodiment are preferably spaced approximately every 0.10 inches around the perimeter of the concentration patch 62. The adhesive force of the material of the adhesive member 65 is preferably more than the force needed to tear the adhesive member at the stress razors 66, so that if the concentration patch 62 is removed, the material of the adhesive member is torn. Thus, when a concentration patch of this preferred embodiment is worn, a torn adhesive member serves as an indication that the wearer has likely tampered with the patch. Of course, the weakening of the adhesive member 65 may be accomplished by providing perforations rather than slits and the slits or perforations may be oriented in directions other than radially.

During storage prior to use, it is desirable to cover the adhesive member to prevent it from sticking to any surface; otherwise the stress razors 66 could become torn prior to use. Accordingly, in the preferred embodiment shown in FIG. 8, the concentration patch is provided with an inner cover 69 to protect the adhesive member 65. The inner cover 69 is removed to expose the adhesive member 65 prior to application of the patch 62 to a subject's skin. Any of a variety of non-adherent materials known to those of skill in the art may be used for the inner cover 69, such as those commonly used to cover adhesive bandages.

The concentration patch 62 is virtually impossible to remove and replace without showing visible signs of tampering. Thus, any analytes in sweat produced from skin under the concentration zone 14 during the time the patch is worn should be present in the patch.

However, a particularly shrewd subject desiring to produce false negative results could obtain additional test patches. This shrewd subject would obtain false negative results by removing the initially applied test patch and replacing the test patch just prior to the time the patch is to be removed for assay. In order to ensure that the patch removed from the subject is the same patch which was initially applied to the subject, an identifying marker which is difficult to reproduce can be incorporated into the patch. For example, a bar code identification strip 67, similar to the bar codes used at supermarket check out stands can be incorporated into the patch, preferably just below the adhesive member 65. For best results in protecting against replacement of the patch, it is important that the identifying marker not be easily removed and replaced without providing and indication that the patch has been tampered with.

In a preferred embodiment, the patch 62 has a filter 68 between the outer layer 65 and concentration zone 14, as described above in connection with FIGS. 1–3a. In a particularly preferred embodiment, the filter is a liquid permeable filter formed from a James River Paper Drape.

The preferred adhesive members of the embodiment shown in FIG. 8, made from adhesive materials, such as Tegaderm, which are relatively weak in strength, have generally been designed for hospital patients who are not expected to perspire at high rates. Therefore, the moisture vapor transmission rate (MVTR) of these materials is relatively low. For example, the MVTR of Tegaderm is approximately 810 g/m*m*day. However, an active person may perspire at instantaneous rates as high as 26000 g/m*m*day. Consequently, an active person may put out more sweat than these adhesive members can transmit to the atmosphere. If this sweat accumulates for any significant period of time, channels may be formed between the skin 64 and the adhesive member 65, allowing sweat to exit between the adhesive member and the skin, rather than be absorbed by the concentration patch 62.

Figure 9:
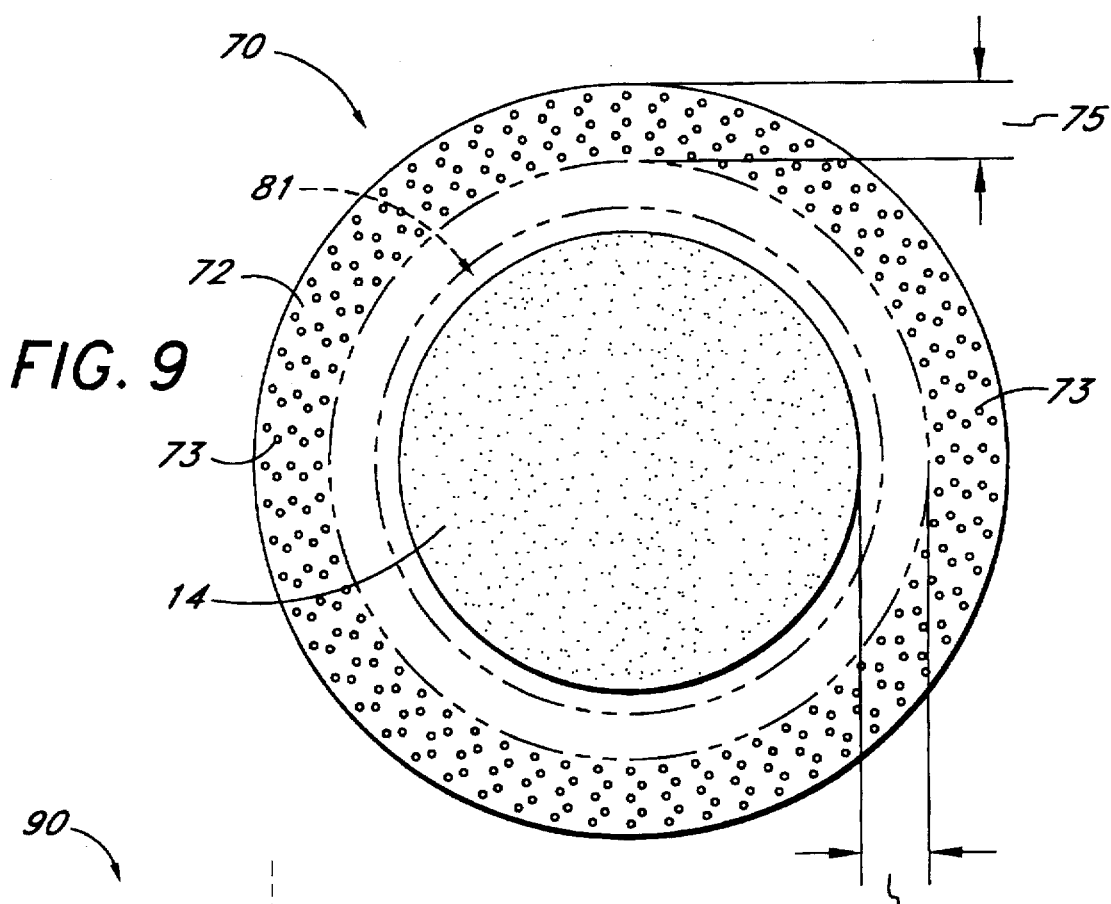
FIG. 9 is a plan view of a dermal concentration patch according to a further embodiment of the present invention.

Thus, in accordance with a further embodiment of the present invention, illustrated in FIG. 9, there is provided a patch 70 having an adhesive member 72 which allows excessive sweat to be freely transmitted to the outside through pinhole perforations 73. The pinhole perforations may be distributed throughout a wide band 75 extending from the outer perimeter of the adhesive member to a narrow band 77 surrounding the test region 821 of the patch 70.

Sweat produced beneath test region 81, over which there are no pinhole perforations 73, will be absorbed by the test region and will not be transmitted to the outside. The test region 81 includes the area of the patch 70 directly under the concentration zone 14 of the patch as well as the area immediately outside this zone. The narrow band 77 outside the concentration zone 14 of the patch has no pinhole perforations 73, and substantially restricts sweat forming underneath the test region 81 from communicating with the wide band 75 where sweat is transmitted to the outside.

The width of the narrow band 77, is preferably between 0.025 and 0.250 inches, more preferably between 0.05 and 0.125 inches. Narrow band widths less than the preferred width are not expected to keep contact with the skin, whereas narrow band widths greater than the preferred width may allow sweat channels to form, creating a path for sweat forming within the test region 81 to communicate with the outside.

A wearer of the patch in screenings for drugs of abuse would be expected to be rather creative in circumventing the protections of the patch. For example, a creative wearer could try to wash out the concentrated sweat components from the patch while the patch remains on the wearer's skin.

Such washing could be attempted using a needle and syringe, such as those commonly used by intravenous drug abusers for drug injection.

For those patches employing specific binding chemistry, attempted elution of the concentrated components using water would likely prove unsuccessful. Even for those patches not employing specific binding chemistry for the analyte being tested, elution with water alone would be difficult, requiring substantial volumes of water without triggering the detection of tampering through the removal of the patch from the skin. However, elution with urine from an animal or non drug user could be successfully used to remove certain analytes from the patch. Additionally, certain analytes could successfully be at least partially eluted using non-aqueous solvents such as acetone, commonly available as nail polish remover.

Thus, in order to detect tampering with the patch through elution of the patch's contents using water or other solvents, a known amount of a marker which is readily soluble in either aqueous or non-aqueous solvents, can be added to the concentration zone during manufacture of the patch. The marker should be easily quantifiable. The marker should also be soluble in either aqueous or nonaqueous solvents depending on the likely route of elution of the analyte. Additionally, the marker should be suitable for prolonged skin contact and not be readily absorbed by the skin. A variety of dyes used in the production of makeup have these suitable characteristics. Oil red N (catalogue number 29,849-2) sold by Aldrich Chemical Corp. of Milwaukee, Wis. is a suitable lipid soluble dye. DG01 red and DH60 yellow, both available from Virginia Dare Extract Co. of Brooklyn, N.Y. are suitable water soluble dyes. These water soluble dyes can be easily quantitated by elution from the patch followed by measuring optical density at 6500 nm for the red or 5800 nm for the yellow dye. The quantity of dye remaining can be compared with the range of the amount of dye found to be remaining in patches worn continuously without tampering for the same length of time.

Non-visible markers could also be used to prevent the wearer of the patch from obtaining feedback regarding the extent of marker remaining in the patch. A colorless protein could be used for this purpose. A protein should be chosen that is easily identified in the lab, and also not be expected in human sweat. For example, Bovine gamma globulins, such as those sold by Sigma Chemical Co. of St. Louis, Mo., could also be used as a marker. The presence of these markers can be easily ascertained using Bovine IgG RID kit, available from ICN of Costa Mesa, Calif.

Thus, when a suitable marker is employed within the concentration patch, when the patch is analyzed for the particular analyte being tested, the patch can also be analyzed for the presence of the marker. For visible markers, such as makeup dyes, the presence of the marker may be analyzed by simply viewing the patch. For non-visible markers, the non-visible marker can be assayed along with the analyte. A significant decrease in the amount of marker present would be an indication of tampering through elution of the patch with a solvent.

A further method of tampering with the patch would be to add an adulterant to the patch which interferes with the assay chemistry. Numerous materials have been used to adulterate urine tests for drugs of abuse. The most commonly used, and generally most effective method of producing a false negative result in a urine test is to dilute the urine by ingestion of excessive amounts of fluids. Advantageously, this approach would not likely be successful in producing false negative results in the sweat collection patch of the present invention because interstial concentration of drug metabolites is less likely to be influenced by ingestion of fluids.

However, the addition of certain adulterants to the patch may interfere with the analysis chemistry. For example, acids and bases are known to interfere with assays for many drug metabolites by altering the metabolites' molecular structure. Additionally, many household products, such as detergents, ammonia, ascorbic acid (Vitamin C), and drain openers have been used to interfere with urine assays. These products all produce extremes of pH and would be expected to result in trauma to the skin if used in connection with tests using the concentration patch of the present invention. This trauma could be noted by the technician removing the patch.

However, weak acids and bases, as well as eye drops sold under the trademark "Visine," are also known to interfere with a variety of assays for drug metabolites in urinalysis. However, these materials would not be expected to produce skin trauma. Thus, the use of these materials or other compounds interfering with an assay that do not cause skin trauma might go unnoticed by the technician removing the patch if the liquid contents of the material have had time to evaporate across the outer layer of the patch. However, "Visine" and most other adulterants would be expected to contain ionic materials.

Thus, in order to detect the use of an adulterant, test strips can be incorporated into the concentration patch which will detect the presence of various ionic materials or of extremes of pH. Litmus paper, such as Hydrion pH test paper, available from Baxter Scientific Products, is well known as an indicator of variances of pH. Accordingly, a short piece, for example 1 cm by ½ cm, of litmus paper could be incorporated into the patch to detect the various household products identified above which are known to be highly acidic or basic.

Many test strips are also known for detecting the presence of ionic materials. For example Baxter Scientific Products supplies test strips from a variety of manufacturers for the detection of each of the following ions: aluminum, ammonium, chromate, cobalt, copper, ion, nickel, nitrate, peroxide, sulphite, tin, and calcium. In addition, test strips sold under the name "Qantab" are available from Baxter Scientific Products which identify the presence of chlorine ions. Other test strips available from the same supplier show glucose, protein, and ketones. Most of these test strips are read by simply comparing the color of the strips with a color chart included with the strips. Thus, the test strips provide a simple method of identifying the introduction of any of a variety of adulterant materials.

In order to detect adulterants, such as "Visine," which contain ionic materials not known to the person performing the test, the tester must first assay the adulterant using a variety of test strips for ions to ascertain which ions are present in the materials. Once the appropriate ions are detected, the test strips corresponding to those ions can be incorporated into the concentration patch in order to provide an indication that the adulterant has been added to the patch.

Curiously, any particular adulterant might produce false negative results in some assays and false positive results in others. For each assay, the common adulterants which could be used to produce false negative results could be identified by testing the assays with the addition of small amounts of these known materials. Test strips could then be included which would detect the addition of these adulterants.

In a preferred embodiment, the test strip or strips are placed facing the skin, where the strips are not visible to the wearer. The wearer is thereby not provided any feedback which aids the wearer in deception.

Many biological compounds are known to be affected by various spectral bands of light energy. For example, urine samples for analysis of LSD must be kept from exposure to strong light. (Schwartz, *Arch. Inter. Med.* 148:2407–12 (1988)). Further examples of compounds which require protection from light include cocaine hydrochloride (*Martindale Extra Pharmacopoeia*, 29th Ed., p. 1213) and morphine sulphate (Id., p. 1310). It is expected that these and other compounds may be affected by exposure to light while being concentrated in the collection patch as well.

Many analytes to be determined by a concentration patch of the present invention may require collection and storage in the patch for prolonged periods of time (up to several weeks). These analytes are, therefore, exposed to substantial quantities of photoradiation. This quantity of photoradiation may be substantially greater than during a urine assay for the same or similar analyte. Also, many analytes have peculiarly high sensitivity to light. Thus, for analytes of peculiarly high photosensitivity or for those requiring prolonged collection and storage, it is particularly important to shield photosensitive analytes from light during prolonged storage in the patch.

Figure 10:
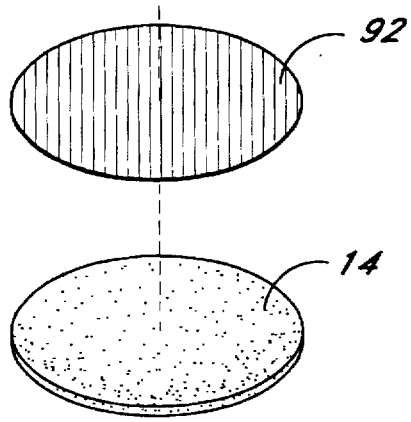
FIG. 10 is an exploded elevational view according to still another embodiment of the present invention.

Accordingly, in still another embodiment of the present invention, illustrated in FIG. 10, there is provided a test patch 90 having a light attenuation layer 92 between the outer adhesive layer 65 and the concentration zone 14. In FIG. 10, the adhesive layer 65, is shown having stress razors 66, however, this feature is to be understood as being optional in this embodiment of the invention.

The attenuation layer 92 is provided in order to attenuate the transmission of light into the concentration zone 14 where the biological compound of interest is being collected and stored. The layer 92 should be substantially impervious to the transmission of photoradiation, yet should also allow relatively unrestricted passage of the aqueous components of sweat to the outer adhesive layer 65. The layer 92 should be of sufficient porosity that diffusion of the aqueous components of sweat occurs at least as rapidly as sweat normally accumulates in the patch.

Because light of many wavelengths is capable of degrading the various biological compounds which may be of interest, the layer 92 should have optical properties which attenuate light throughout a wide spectrum. Attenuation can be achieved by either reflection or absorption of incoming light. Reflection may be achieved through, for example, the use of any of a variety of metallic surfaces. When used in accordance with certain preferred embodiments of the present invention, the attenuation layer 92 should allow passage of aqueous components of sweat. In order to provide a reflective layer with the suitable permeability, thin metallic foil with small holes can be provided. For example, aluminum foil, commercially available from many sources including Reynolds Aluminum Co., could be perforated with a plurality of small holes. Absorptive attenuation layers can be provided through the use of a black surface. Preferably, these surfaces would continue to allow permeability of aqueous components of sweat. It is important that any dye or pigmentation in the attenuation layer 92 not bleed when exposed to the aqueous components of sweat and also that it not interfere with any binding chemistry or in the analysis of the analyte. Any of a variety of thin black papers having these properties are commercially available and are suitable for use as in the attenuation layer. For example, black Deltaware cellulose membrane filters available from Baxter Scientific Products have been found to be especially useful for use as an attenuation layer. This product is available in a variety of porosities; more open pores are preferred. Thus, in the preferred embodiment, 0.6 micron black Deltaware filters are provided.

In an alternative to the provision of an attenuation layer (not shown), the adhesive layer 65 can be made to attenuate light, either through absorption or reflection. As an example of an absorptive adhesive layer, black colorant, such as fine carbon black powder, could be incorporated into the extrusion of the adhesive sheet.

The following examples describe only specific applications of the present invention.

EXAMPLE 1

Preparation of Microbead Test Patch

One specific application of the present invention is the dual determination of skeletal muscle and cardiac muscle status as a result of exercise. A dermal concentration patch is constructed in accordance with the embodiment illustrated at FIGS. 3 and 3a. The gauze layer is prepared by cutting a circular patch having an approximately 1-inch diameter from a Johnson & Johnson non-stick gauze pad. The inner and outer porous layers are next prepared by cutting two circular patches of Ultipor (nylon 6), from Pall Corporation in Glen Cove, N.Y. Ultipor membrane is both liquid permeable and microporous, and a membrane is selected having, for example, a 1 micron rating. The microbead layer is prepared by covalently bonding monoclonal antibody raised against CK-MB to a multiplicity of polystyrene beads having a mean particle size of at least about 10 microns.

The concentration patch is assembled by distributing approximately 0.2 gram of microbeads across the surface of one of the porous layers. The second porous layer is thereafter disposed adjacent the microbeads, and the gauze layer is next placed on top of the second porous layer. At this point, the patch is upside-down. The peripheral edges of each of the first and second porous layers and the gauze layers are secured together by conventional heat-sealing techniques. Thereafter, the subassembly is turned over and an annular torus of adhesive tape having approximately a 2-inch outside diameter and slightly less than a 1-inch inside diameter is secured thereto to produce a finished concentration patch.

EXAMPLE 2

Cardiac Muscle Status Test

The concentration patch of Example 1 is then secured to the chest of a healthy 40-year old male and worn throughout a 36-mile (130-minute) bicycle ride. Upon removal of the concentration patch following the ride, the test patch is immersed in a first solution containing an excess of enzyme labeled anti-CK-MB for approximately 30 minutes, to permit conjugation of labeled antibody with immobilized analyte. The patch is then rinsed under tap water to remove unbound labeled antibody and immersed in a second solution containing a substrate for the bound enzyme label, which undergoes a color change when acted upon by the enzyme. Appearance of color through the top porous layer indicates the presence of CK-MB, and possible cardiac injury. Comparison to a color chart permits rough quantification.

EXAMPLE 3

Test for Use of Marijuana

THC polyclonal antibody from sheep (available from Biogenesis, Bournmouth, England) is diluted 1:100 in PBS (pH 7.5). The antibodies are bound to Gelman 0.45µ (SU-450) Ultrabind Supported Membrane, following the protocol in Gelman Original Equipment Manufacturer application P.N. 31,084. The membranes are air dried. Disks, 3/8 inch in diameter, are cut from the coated Gelman membranes. These 3/8 inch disks are mounted at the center of a 1/4 inch diameter hole cut in the center of a one inch diameter circle of Tegaderm 1625 Transparent Dressing (available from Minnesota Mining and Manufacturing, St. Paul, Minn.).

Three mounted membranes are secured to the chest of a subject who then smokes a marijuana cigarette. Three mounted membranes are also secured to a subject who has never used marijuana in any form and who agrees not to use it for the next seven days. The membranes remain in place until they are removed, seven days later. Each of the removed membranes is flushed five times with 300 µl of 0.2% Tween 20 in PBS. The membranes are incubated for 30 minutes in 100 µl of E-Z Screen Cannabinoid enzyme conjugate from the E-Z Screen Test Kit (available from Environmental Diagnostics, Inc., Burlington, N.C.).

After incubation, each membrane is flushed three times with 300 µl of 0.2% Tween 20 in PBS, followed by three flushes with PBS alone. The membranes are then incubated in TMB Membrane Peroxide Substrate (available from Kirkegaard & Perry Labs, Gaithersburg, Md.) for 10 minutes. A light blue background appears in all six membranes. White dots appear over the background on the three membranes taken from the subject who smoked a marijuana cigarette, indicating sweat gland output of sweat containing THC derivatives. No white dots appear on the three membranes taken from the subject who has never used marijuana.

EXAMPLE 4

Positive Control Patch

Mouse anti-human IgG, Fc monoclonal antibody (available from ICN, Costa Mesa, Calif.) is diluted 1:100 in PBS (pH 7.5). The antibodies are bound to Gelman 0.45µ (SU-450) Ultrabind Supported Membrane, following the protocol in Gelman Original Equipment Manufacturer application P.N. 31,084. The membranes are air dried. Disks, 3/8 inch in diameter, are cut from the coated Gelman membranes. These 3/8 inch disks are centered and mounted on a 1/4 inch diameter hole cut in the center of a one inch diameter circle of Tegaderm 1625 Transparent Dressing.

Three mounted membranes are secured to the chest of five human subjects. The membranes remain in place until they are removed, seven days later. Each of the removed membranes is flushed five times with 300 µl of 0.2% Tween 20 in PBS. The membranes are incubated for 30 minutes in 100 µl of Horseradish peroxidase enzyme conjugated to goat anti-human IgG, Fc polyclonal antibody (available from ICN, Costa Mesa, Calif.) diluted 1:1000 in PBS.

After incubation, each membrane is flushed three times with 300 µl of 0.2% Tween 20 in PBS, followed by three flushes with PBS alone. The membranes are then incubated in TMB Membrane Peroxide Substrate (available from Kirkegaard & Perry Labs, Gaithersburg, Md.) for 10 minutes. Blue dots corresponding to individual sweat ducts appear over the background on all of the membranes, indicating that the chemistry of the patches is operative by their detection of the IgG expected in the sweat of all subjects.

Although invention has been described in terms of certain preferred embodiments and immunoassay schemes, other embodiments and immunoassays that are apparent to those of ordinary skill in the art are also within the scope of this invention. Accordingly, the scope of the invention is intended to be defined only by reference to the appended claims.

I claim:

1. A dermal concentration patch for determining the presence of a photosensitive analyte in a subject mammal's perspiration, comprising:

a concentration layer having a first side and a second side;

an attenuation layer disposed over the second side of the concentration layer for attenuating the amount of light reaching the concentration layer; and an adhesive membrane on at least one of the concentration layer or attenuation layer for securing the first side of the concentration layer in fluid communication with the subject's skin, wherein water vapor is permitted to escape through the concentration layer and the attenuation layer and outside of the concentration patch.

2. The concentration patch of claim 1, wherein the light attenuation layer comprises black paper.

3. The concentration patch of claim 1 wherein the attenuation layer comprises a light reflective material.

4. The concentration patch of claim 3, wherein the attenuation layer comprises a metallic surface.

5. The concentration patch of claim 4, wherein the attenuation layer comprises aluminum foil perforated with a plurality of holes.

6. The concentration patch of claim 1 wherein the attenuation layer comprises a material capable of substantially absorbing incoming light energy.

7. The concentration patch of claim 6, wherein the attenuation layer comprises a dark surface.

8. The concentration patch of claim 1 wherein said concentration layer additionally comprises a specific binding partner for said analyte.

9. The concentration patch of claim 8, wherein said specific binding partner is an antibody.

10. A dermal concentration patch for determining the presence of a photosensitive analyte in a subject mammal's perspiration, comprising:

a water permeable support layer having a first side and a second side; and a vapor permeable attenuation layer on the second side of the support layer for attenuating the amount of light reaching the support layer, the attenuation layer having an adhesive thereon for securing the first side of the support layer in fluid communication with the subject's skin, wherein water is permitted to escape through the support layer and outside of the concentration patch.

11. A dermal concentration patch for determining the presence of a photosensitive analyte in a subject mammal's perspiration, comprising:

a concentration zone for collecting and storing said photosensitive analyte, wherein said concentration zone has a first side and a second side, wherein said first side is capable of being placed in fluid communication with the subject's skin;

an adhesive layer having a first side and a second side, wherein said first side is proximate to said second side of said concentration zone, for removably securing the first side of said concentration zone in fluid communication with the subject's skin; and an attenuation layer having a first side and a second side, wherein said first side is proximate to said second side of said adhesive layer, for attenuating the transmission of light into said concentration zone, wherein the concentration zone and the attenuation layer allow passage of aqueous components of sweat to outside of the concentration patch.

12. A method of determining the presence of a photosensitive analyte in perspiration of a subject mammal, comprising the steps of:

securing a dermal patch having a concentration zone to the subject's skin, wherein said concentration zone is in fluid communication with the subject's skin;

collecting perspiration containing said photosensitive analyte from said subject's skin in said concentration zone;

attenuating the amount of photoradiation reaching said concentration zone during said collecting step, thereby protecting said photosensitive analyte from excessive photoradiation exposure;

concentrating said photosensitive analyte in said concentration zone by allowing aqueous components of perspiration to pass through and escape from said dermal patch; and determining the presence of said photosensitive analyte in said subject's perspiration.

13. The method of claim 12, wherein said attenuating step is accomplished by placing a substantially nontransmissive layer over the concentration zone of said dermal patch.

14. The method of claim 12, wherein said dermal patch comprises an adhesive layer, and wherein said securing step comprises adhering said adhesive layer to said subject's skin.

15. The method of claim 14, wherein said attenuating step comprises placing a reflective material proximate to said adhesive layer of said dermal patch.

16. The method of claim 13, wherein said substantially nontransmissive layer is a metallic material.

17. The method of claim 12, wherein said attenuating step comprises placing a material capable of substantially absorbing light proximate to said concentration zone of said dermal patch.

18. The method of claim 14, wherein said attenuating step comprises placing a material capable of substantially absorbing light proximate to said adhesive layer of said dermal patch.

* * * * *